Figure 1:
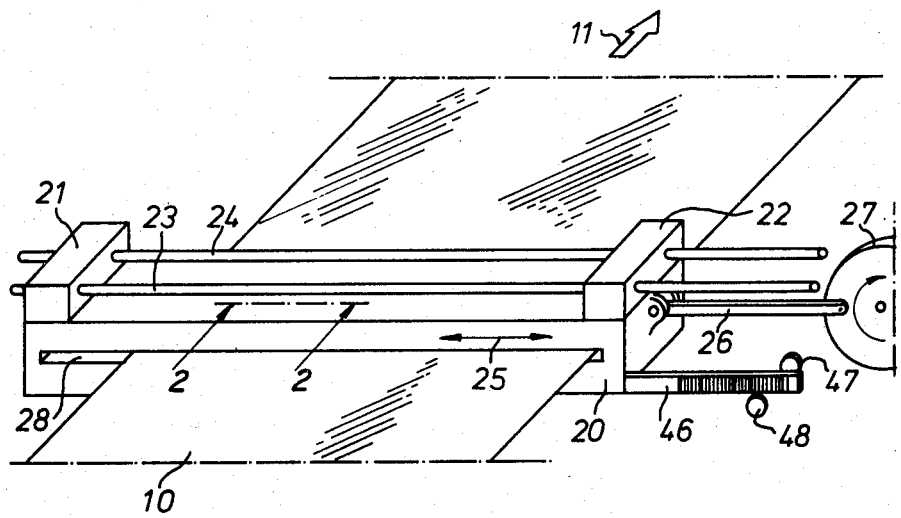

United States Patent [19]

Burtin et al.

[11] 4,274,748
[45] Jun. 23, 1981

[54] METHOD AND DEVICE FOR INSPECTING A MOVING SHEET MATERIAL FOR STREAKLIKE DEFECTS

[75] Inventors: Jean Burtin, Mol; Maurits Geens, Haacht, both of Belgium

[73] Assignee: AGFA-GEVAERT N.V., Mortsel, Belgium

[21] Appl. No.: 85,711

[22] Filed: Oct. 17, 1979

[30] Foreign Application Priority Data

Oct. 19, 1978 [GB] United Kingdom ............... 41163/78

[51] Int. Cl.³ ........................................... G01N 21/89
[52] U.S. Cl. .................................. 356/431; 250/563; 250/572; 356/239
[58] Field of Search ............... 356/429, 430, 434, 239, 356/444; 250/563, 572

[56] References Cited

U.S. PATENT DOCUMENTS 4,005,281   1/1977   Faulhaber et al. ............. 356/239 X Primary Examiner—John K. Corbin
Assistant Examiner—Bruce Y. Arnold
Attorney, Agent, or Firm—William J. Daniel

[57] ABSTRACT

Subtle streaklike defects in running webs and sheets are identified by transversely scanning adjacent lateral sections of the webs or sheets by means of radiant energy means. Transmitted or reflected radiation is received on corresponding photocells that produce measurement signals that are representative of a defect in the webs or sheets. The signal-to-noise ratio of the measurement signals is increased by multiplicative correlation, on the condition that the ratio of the signal component $V_d$ to the effective noise component $V_n$ of the measurement signal $V_m$ is greater than one.

10 Claims, 13 Drawing Figures

U.S. Patent  Jun. 23, 1981  Sheet 1 of 6  4,274,748

GV 1031

METHOD AND DEVICE FOR INSPECTING A MOVING SHEET MATERIAL FOR STREAKLIKE DEFECTS

This invention relates to a method and a device for inspecting a moving sheet material for streaklike defects, comprising means for directing radiant energy on one surface of the sheet material and photocell means for measuring at distinct lateral positions across the sheet material the intensity of the radiation after transmission of the radiation through, or after reflection on the surface of the sheet material.

Known devices operate satisfactorily for the detection of rather coarse speck- and streaklike defects in moving sheets since in these cases the signal-to-noise ratio of the output signals of the photocells is sufficiently great to enable the signals, after their amplification, to be compared with a predetermined reference signal in order to identify a defect. Suchlike defect indentifying signals may either be stored in digital or analogue form in a memory together with the exact location of the defect, or they may directly be signalled as in the coating of webs in order to arrest or to readjust the coating, or they may directly control a sorting mechanism as in the inspection of sheets out from a coated web. As examples of rather coarse defects can be mentioned specklike defects caused by the inclusion of a foreign object, e.g. a dust particle in a coated layer, or a dry spot, e.g. an air bubble included during the coating of a layer on a support.

In those cases, however, where very minute defects have to be identified, fluttering of the material at the place of measurement and noise of the electronic circuitry may cause variations in the output signals of the photocells that are of the same order of magnitude as those caused by a sheet defect itself.

It is known to use electronic correlation techniques for improving the signal-to-noise ratio, hereinafter referred to as S/N ratio, of the defect identifying signals. A basic condition for the operation of such techniques is that the defect to be identified should be recursive during a number of, say at least 5, successive scans. This means that the defects have to be of protracted duration in the machine direction, that is in the coating direction in the case of the inspection of coated layers. In other words, only streaklike defect signals are suitable for S/N ratio improvement.

The use of additive correlation in apparatus for the inspection of moving webs is disclosed for instance in GB-P No. 1,471,316 of E. Kodak and in U.S. Pat. No. 4,005,281 of E. I. Du Pont de Nemours and Company. The mentioned use does not provide results that are entirely satisfactory for the following reasons.

The S/N ratio improvement that can be obtained is rather limited as will be further explained in detail in the description of the invention. For instance, for a gain A in the feedback loop of a delay line equal to 0.90, the S/N gain is 12.78 db whereas for A=0.99, the gain is 22.98 db in accordance with the formula:

$$S/N \text{ (in } db\text{)} = 20 \log \sqrt{\frac{1+A}{1-A}}.$$

Further, whereas it is possible to use for a factor A=0.90 an analogue circuitry, the use of a factor A=0.99 inevitably necessitates the use of a digital circuitry in order to obtain a sufficient accuracy, and suchlike digital arrangement requires a rather extensive hardware layout.

Finally, the time t of the correlation circuit for reaching a significant S/N ratio improvement is rather important so that in some cases it may take up to 100 seconds and more before the correlated signal is available. It is the object of the invention to provide a new correlation technique in the inspection of a moving sheet material for streaklike defects, that does not show the shortcomings mentioned hereinbefore. The invention aims in particular at considerably improving the S/N ratio of photocell signals that are encountered in the identification of very subtle streaklike defects in moving sheet materials.

As an example of very subtle streaklike defects, streaklike irregularities may be mentioned that occur at the coating on a web of a layer, or of a combination of layers as the case may be, by means of a so-called cascade of slide hopper coater. In certain application fields, notably in photography, very stringent requirements are put to the uniformity of a coated layer, and it is shown that defect signals resulting from streaklike thickness deviations of an order of magnitude under 0.1%, even when additively correlated, are not discernable from the noise component of the signals.

As to the occurrence of the mentioned defect in the said coating technique, it is assumed that the most important cause for such defect is the passage of a web splice through the coating bead. It appears that a web splice entrains air in the coating bead and that such air may remain there for quite long periods, in some circumstances covering hundreds of meters of material, so that the coating thickness at that area is correspondingly disturbed.

Considering the fact that in the manufacture of delicate materials, such as for instance radiographic film or film for graphic reproduction techniques, thickness deviations in coated layer in the order of magnitude of 0.1% and preferably even less than 0.1% should be indentified, it will be understood that the signal-to-noise characteristics of common detection systems do not enable a reliable and rapid identification and retrieval of the mentioned defect.

In accordance with the present invention, a method for inspecting at least the longitudinal section of a moving sheet material for streaklike defects, by repeatedly transversely scanning said at least one section of the material by means of radiant energy capable of being modulated by said sheet material, and by receiving said modulated energy on at least one photocell thereby to detect at said at least one photocell signals that are periodically recurring in response with the transverse scanning of the material and vary as an indication of the presence of said defects, comprises improving the S/N ratio of those said periodically recurring signals having a S/N ratio greater than one, by delaying each measurement signal $V_m$ over a delay time period t corresponding with the scanning period P, multiplying a next signal $V_m$ with a factor that is proportional to the product of said delayed signal and a factor A, delaying said multiplied signal over said delay time t multiplying the next signal $V_m$ with a factor that is proportional to the product of said previous multiplied signal and said factor A, and so on for a number of times, wherein said factor A is at least equal to one, and wherein the relationship $V_m \cdot A > 1$, applies where signal $V_m$ is expressed in volts.

The notion "streaklike defect in a moving sheet material" stands in the present statement for a line-wise defect that runs parallel with the direction of movement of the sheet material during its inspection.

The term "sheet material" stands for webs that may have a length up to many hundreds of meters, as well as for a plurality of distinct sheets that may have been cut from such webs and that may be inspected in succession.

The term "modulated by" indicates that radiation is attenuated on its path towards the photocell, either by transmission through the sheet material or by reflection from the surface of said sheet material. Any defects present modify the attenuation.

The expression "signals with a S/N ratio greater than one" means in the present specification signals in which the defect-component is greater than the effective noise component. This means that peak-to-peak noise levels may be present in the photocell signal that are much greater than the useful signal level but the effective value of which, that is the rms value determined over a time that is equal to the quotient of the scanning time t divided by the number of discrete measurements during said time.

The scanning period "P" is the time comprised between two successive scans of a given zone of at least one longitudinal section from edge to edge in one direction.

The measurement signal $V_m$ may be the output signal of a photocell that must be compared with a given reference signal in order to establish the occasional deviation of the measurement signal, thereby to detect a defect at the lateral position of the sheet material inspected by the photocell, but the signal $V_m$ may also be, and in a different embodiment preferably is, the difference, amplified as the case may be, between two successive signals of a multiplicity of sequential output signals that represent the scanning of the sheet material.

The term "scanning" stands for the repeated inspection of the sheet material in a direction that runs transverse with respect to the direction of movement of the sheet material. The scanning may occur by means of a beam of radiation that is projected on the sheet material and that is swept over the material. This sweeping may be done by means of a source of radiation mounted on a frame arranged for oscillation transverse with respect to the material, but the sweeping may also be carried out by means of a beam of radiation that is deflected by a rotating or pivoting mirror or the like. Alternatively, the scanning may occur by means of a plurality of distinct small light sources, for instance light emitting diodes (LED's) that are mounted closely adjacent to each other in a row and that may be energized in sequence to produce a radiation spot that scans the sheet material.

The photocell may be arranged for lateral displacement in synchronism with the scanning beam of radiation, but the photocell may also collect, for instance by means of a collecting glass rod that extends transversely of the sheet material, the radiant energy that has been modulated by the sheet material. Alternatively, a plurality of photocells may be mounted in a row extending transversely of the web path for receiving radiant energy that has been modulated by the zone of the sheet section that corresponds with the field angle of a corresponding photocell.

According to a preferred embodiment of the invention, a multiplicity of successive measurements are carried out during each scanning, each two successive measurement signals are compared with each other, and the difference between each such two successive signals constitutes the signal $V_m$.

A device in accordance with the present invention comprises:

radiant energy means and photocell means arranged for periodically scanning said moving sheet material, means for amplifying the measurement signals $V_m$ that are produced during the scanning of the sheet material, delay lines controlled in response to the scanning of the material for delaying each measurement signal $V_m$ over a period equal to the scanning period P, multipliers for multiplying each delayed signal $V_m$ with the instant signal $V_m$ that occurs after each said delay period, and for repeating such multiplication for a number of times thereby to increase the S/N ratio of measurement signals which have a signal component $V_d$ greater than the effective noise component $V_n$, means for processing said signals $V_d$ with improved S/N ratio thereby to identify streaklike defects in the sheet material.

Figure 2:
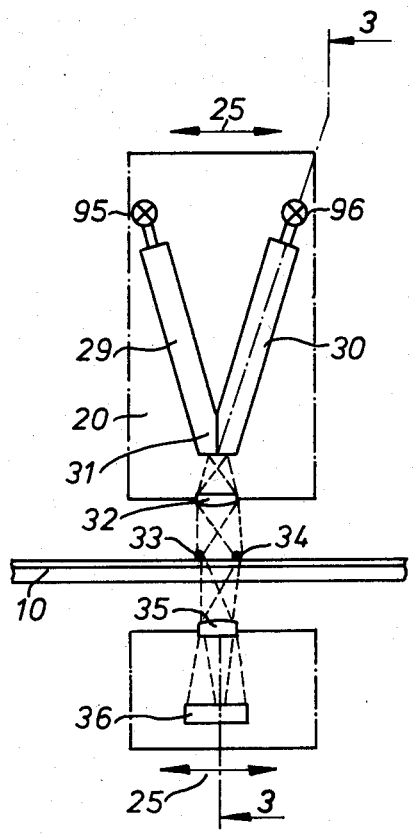
Figure 3:
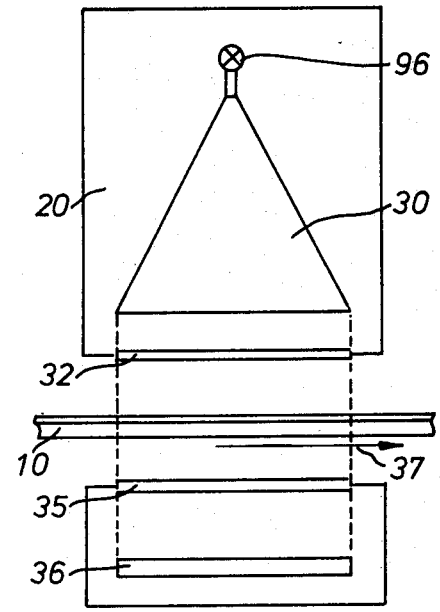
Figure 4:
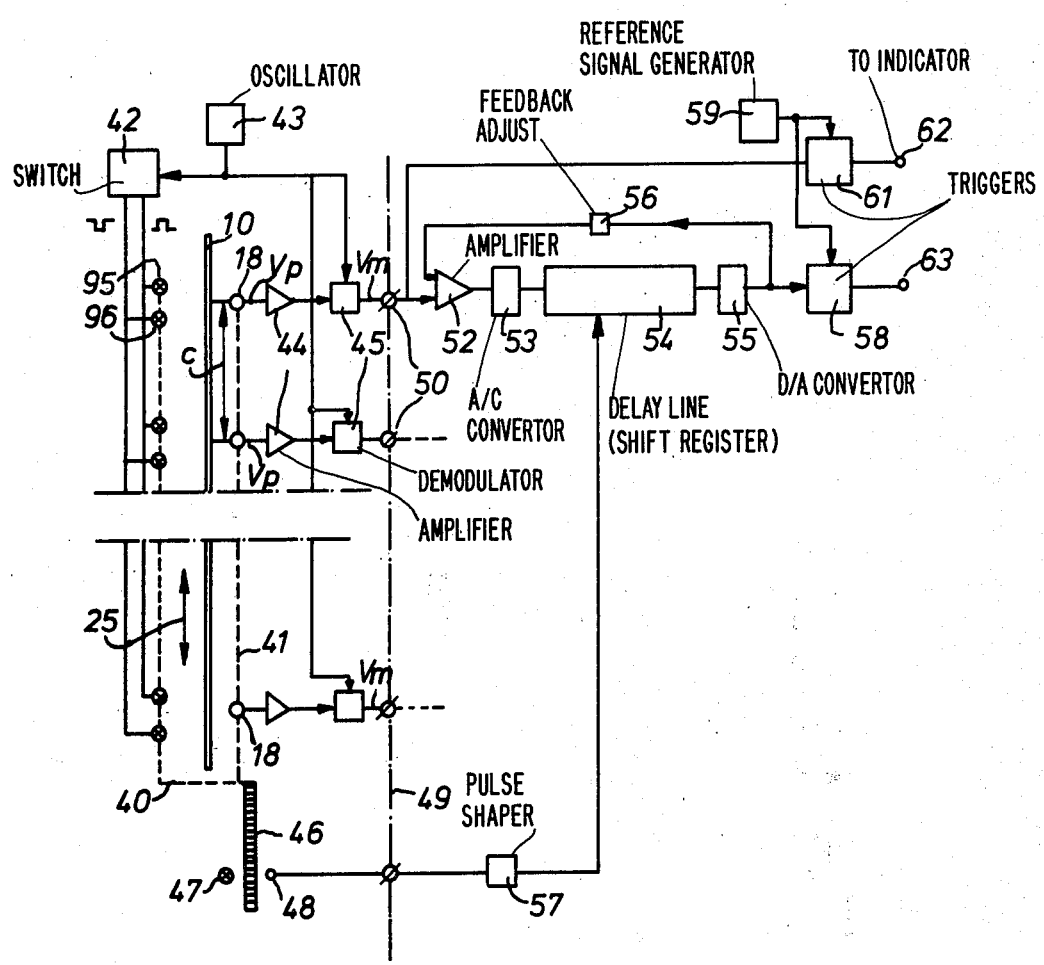
Figure 5:
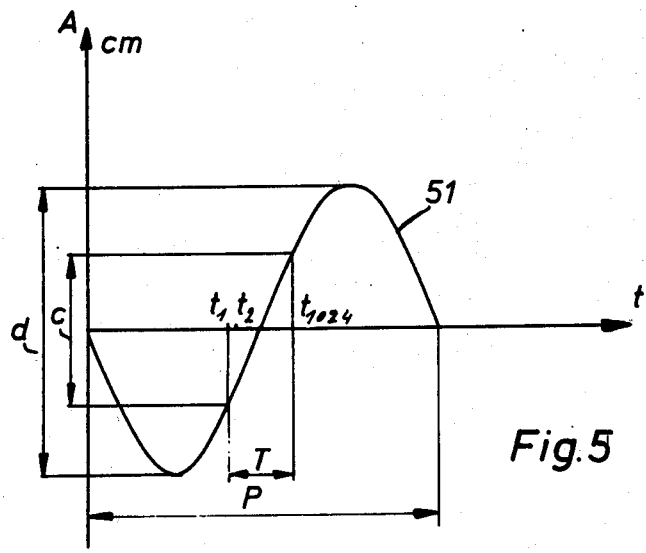
Figure 6:
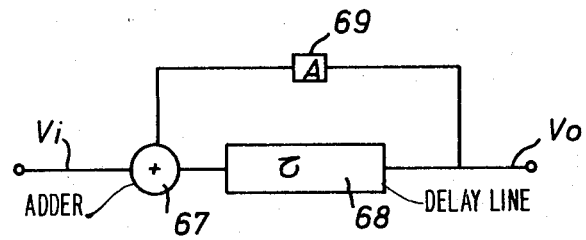
Figure 7:
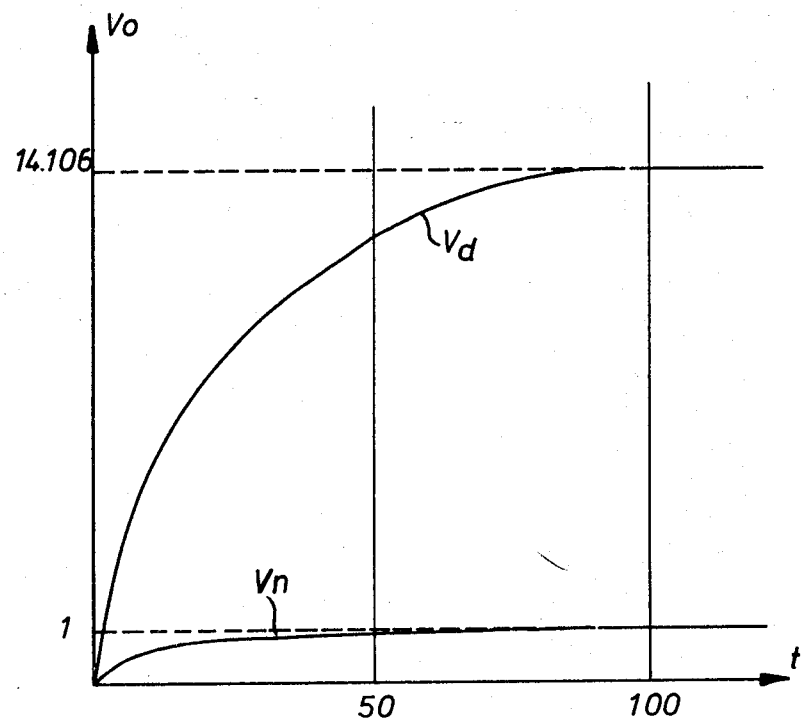
Figure 8:
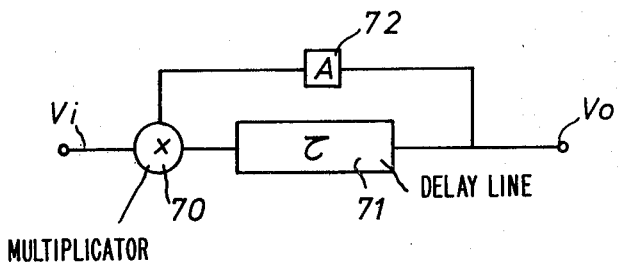
Figure 9:
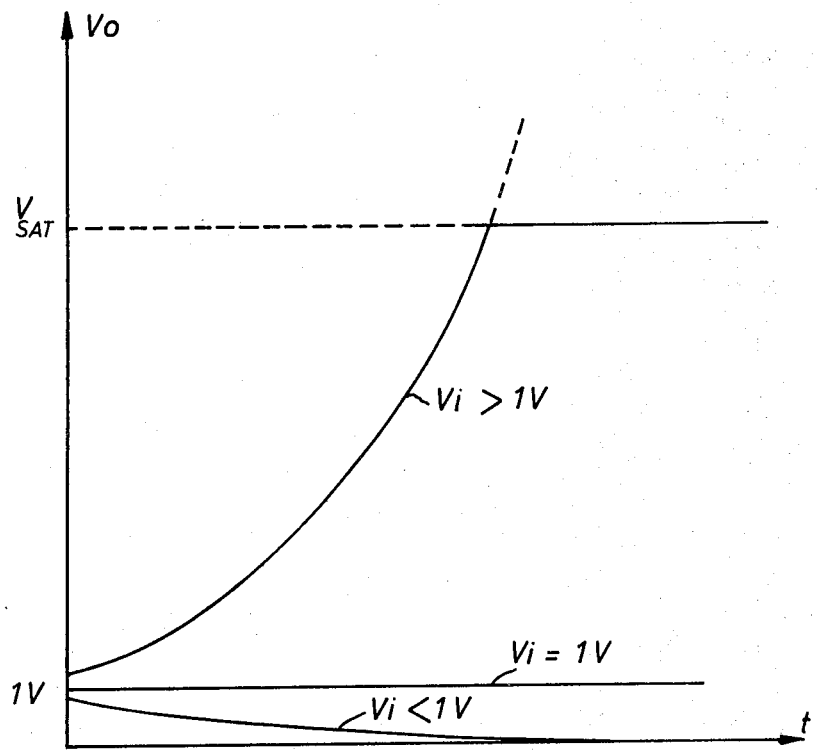
Figure 10:
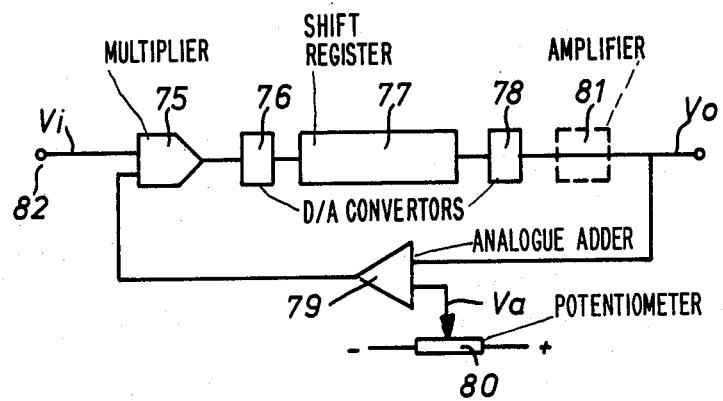
Figure 11:
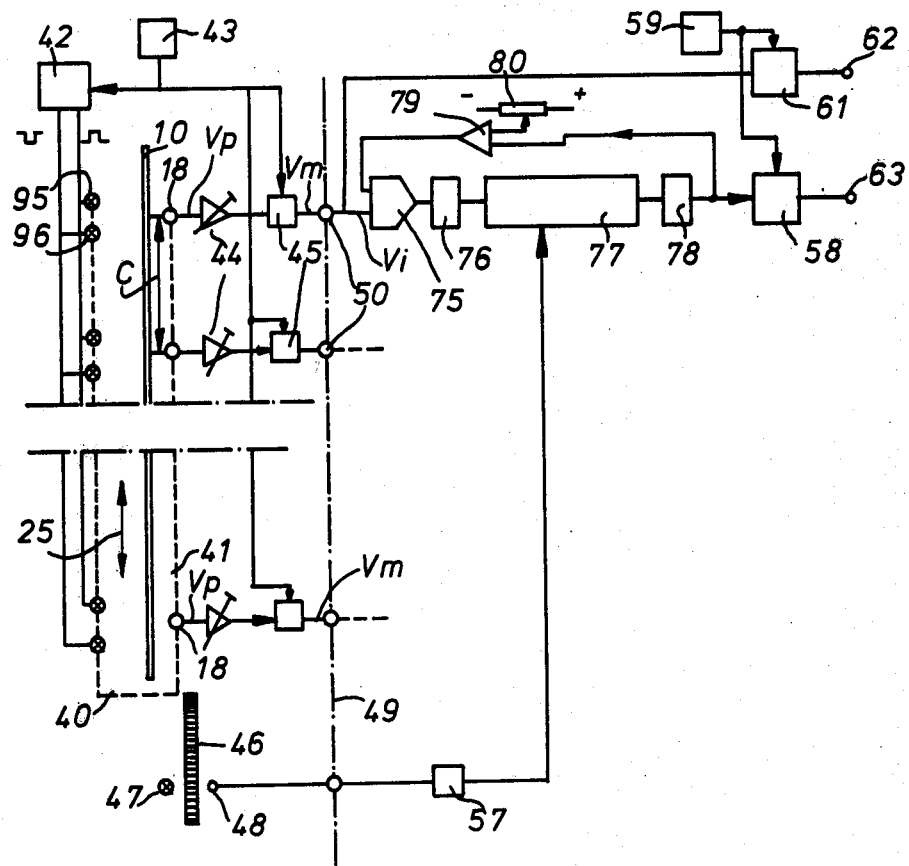

The invention will hereinafter be described by way of example with reference to the accompanying drawings, in which:

FIG. 1 is a diagrammatic isometric view of an embodiment of a device for transversely scanning a moving web, FIG. 2 is a vertical section on line 2—2 of FIG. 1, FIG. 3 is a section on line 3—3 of FIG. 2, FIG. 4 is the electronic block circuit of the device according to FIGS. 1 to 3, and FIG. 5 illustrates the sinusoidal displacement of the device according to FIG. 3, and the operative detection zone within said sinusoidal displacement, FIG. 6 is the basic block circuit of an additive correlator, and FIG. 7 is a diagram illustrating the S/N ratio improvement of the correlator of FIG. 6, FIG. 8 is the basic block circuit of a multiplicative correlator, and FIG. 9 is a diagram illustrating the S/N ratio improvement of the correlator of FIG. 8, FIG. 10 is a more detailed block circuit of the multiplicative correlator of FIG. 8, and FIG. 11 is the electronic block circuit of one embodiment of a device according to the present invention.

Figure 12:
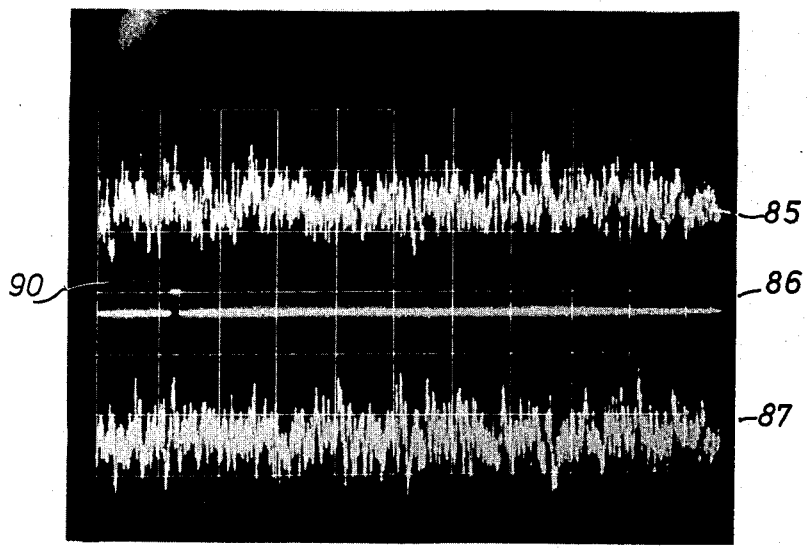
Figure 13:
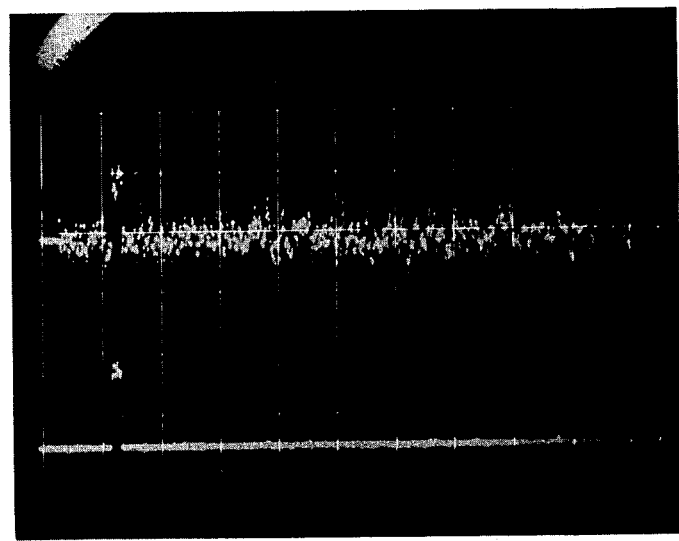

FIG. 12 is a representation of the screen of an oscilloscope showing a noise signal, a defect signal and the combination of both signals, and FIG. 13 is a representation similar to FIG. 12 comparing the improvement in the S/N ratio of the same combined signal by additive or multiplicative correlation, respectively.

FIG. 1 is a diagrammatic isometric view of a device for transversely scanning a moving web. The device comprises a boxlike frame 20 that is slideably suspended by means of two guides 21 and 22 on two horizontally spaced, fixed parallel rods 23 and 24.

It will be understood that the illustrated suspension means may be replaced by any known other suspension or guide mechanism that enables the frame to carry out a scanning movement in the direction indicated by the arrow 25.

The transverse position of the frame with respect to a web 10 that is advanced in the direction of the arrow 11 is controlled by a crank arm 26 that is pivotally fitted to one end of the frame and to a drive wheel 27 that may continuously rotate at a constant speed. The web 10 is passed through the device through a slotlike opening 28 along a path that is determined by the tangent plane to two rollers (not shown), one being located upstream and the other downstream of the device.

Within the device there are mounted several detection units next to each other at equal intervals, each covering a section of the width of the web. One such unit is diagrammatically illustrated in the vertical cross-sectional view of FIG. 2, and the vertical longitudinal sectional view of FIG. 3.

The unit comprises two so-called fishtail optics 29 and 30 which are fiber optic assemblies wherein the fibers are bundled at one extremity to a bundle with a circular cross-section, and wherein the fibers diverge towards the other extremity to form a line on which the single fibers are ranged closely adjacent to each other. The two fishtail assemblies have been ground at their lower ends to form an interface 31 at which they are adhered to each other. A rodlike lens 32 with a semicircular cross-section projects the lines of radiation at the lower ends of the fishtail optics on the web in the form of the two narrow elongate beams of radiant energy hereinafter called "lines", that have been represented by the solid points 33 and 34, respectively. The radiant energy may be produced by any suitable source such as an incandescent bulb, a light-emitting diode (LED), or the like. In the present case, two LED's 95 and 96 were placed to face the upper ends of the corresponding fishtail optics.

Radiation from both lines 33 and 34 that is transmitted through the web may be condensed by a second rodlike lens, such as lens 35 onto an elongate photocell 36. The sources of radiation as well as the photocell carry out an oscillating motion as indicated by the arrows 25. The amplitude of said oscillation is that of the oscillating amplitude of the frame 20 shown in FIG. 3.

It should be noted that several units such as the one illustrated in FIG. 2 are mounted at equal distances next to each other within the frame 20, and that the distance between two successive units is smaller than the amplitude of oscillation of the frame in order to completely transversely scan the web. While the web moves away from the reader according to the illustration of FIG. 2, the web moves towards the right according to FIG. 3, as indicated by the arrow 37.

The electronic block circuit of the device is shown in FIG. 4. A web 10 that moves in a direction normal to the plane of the drawing is scanned by pairs of light sources 95 and 96 that produce adjacent pairs of lines of radiant energy on the web as shown in detail in FIG. 2. Corresponding photocells 18 receive the radiation transmitted through the web and are bodily coupled as illustrated by the broken lines 40 and 41 with the light sources in order to carry out an oscillating displacement with respect to the web in the direction of the arrow 25.

Both light sources of each pair of sources are alternatively energized by a source 42 in response to an oscillator 43. The output signals $V_p$ of the photocells are amplified by amplifiers 44 and synchronously demodulated by corresponding demodulators 45 that are likewise controlled by the oscillator 43. The amplifiers 44 may comprise a high-pass filter with a breakpoint at 20 Hz for 6 db attenuation.

The frame of the device is further provided with a pulse-generator 46 in the form of a glass strip carrying a great number of spaced fields capable of periodically absorbing the radiation from a stationary light source 47 that is directed to a photocell 48. The vertical dash and dot line 49 represents a wall of the oscillating frame on which all electric terminals 50 may be grouped for connection by means of a flexible cable comprising different separate conductors with the remaining electronic circuit of the device which in practice is mounted in a stationary column beside the oscillating frame.

It will be clear that upon oscillation of the frame 20 with the light sources and the photocells, no electric measurement signals $V_m$ occur at the terminals 50 if a defect-free web is being examined. As a matter of fact, the blocklike energizing of the pairs of light sources 95 and 96 produces output signals of the photocells which have equal magnitude, polarity and width so that synchronous demodulation of them by the circuits 45 produces a zero output voltage. When, however, a pair of light sources scan a streaklike defect, the amplitude of the successive output signals of the corresponding photocell will no longer be equal for the two light sources during their passage over a line defect of the web so that the resulting demodulated signal will no longer be zero. The same is true for the other pairs of light sources and the corresponding photocells that each cover a section of the width of the web, as indicated by the distance c.

In connection with this distance c, it should be noted that this is a fraction only of the peak to peak amplitude of the oscillation of the frame 20. This is illustrated in the diagram of FIG. 5 wherein the distance d represents the peak to peak amplitude of the frame 20, whereas the distance c represents the effective scanning width of each photocell. As a consequence of the mentioned difference between d and c, the distance c covers a portion of the curve 51 (that represents the sinusoidal motion of the frame) within which the curve deviates very little from a line, whereby the corresponding speed of the frame during the inverval of measurement is nearly uniform.

As a consequence of the frame amplitude d that is greater than the distance c between two adjacent measuring units, overlapping measurement occurs. The electronic circuit is, however, so arranged (not shown) that the output signals of overlapping measurements of adjacent web sections are not processed.

The right hand portion of the drawing of FIG. 4 shows a known additive correlation circuit for improving the S/N ratio of the measurement signals $V_m$. It should be noted that actually there is one such correlation circuit for each photocell circuit.

The electronic correlation circuit comprises an addertype amplifier 52, an analogue to digital converter 53, a delay with 54 in the form of an 8 bit shift register with 1024 positions, a digital to analogue converter 55, and a feedback element 56. The adder sums the incoming signals $V_i$ with a delayed output signal $V_o$ which has been multiplied by a feedback gain which is strictly less than unity. The delay line 54 is controlled in synchronism with the scanning of the web by pulses produced by the pulse generating strip 46 that comprises in this specific embodiment 1024 pairs of light absorbing and light transmission areas. The signals of the photocell 48 are appropriately shaped by a pulse shaper 57.

The operation of the circuit is as follows. An input signal that occurs at a time $t_1$, see FIG. 5, is stored in the first stage of the shift register 54 until at a time $t_2$ the pulse generator 46 controls the shift register to shift its information over one place whereby the first signal is transferred to a second position, and the new signal that occurs at the time $t_2$ is entered into the shift register. The same procedure continues until the generator 46 has been displaced over a distance c at the time $t_{1024}$ at which point the scanning of the respective section of the web has been completed.

The circuit is so arranged (not illustrated) that during the returning movement of the frame the shift registers remain inoperative. At the second scanning of the web, a pulse from the generator 46 at a time $t_1$ transfers the signal to the shift register that is at the position 1024 to the position 1 whereby (through 55, 56, 52 and 53) said signal is added to the next signal that occurs at the same transverse zone of the web as the zone where said transferred signal occurred, etc. The same operation is repeated a number of times thereby to increase the S/N ratio of each of the signals at the positions from 1 to 1024 by a factor as will further be explained.

The output signals $V_o$ of each correlator circuit are fed to a trigger 58 where they are compared with a reference signal from a reference signal generator 59. In case the difference between both signals exceeds a predetermined value, the output signal at terminal 63 may, either directly control a warning mechanism, or it may be stored either in analogue or in converted digital form in a memory together with the exact coordinates of the location of the defect on the web. One part of said coordinates is formed by the pulse number of the generator 46 which indicates the transverse location of the defect on the web. Another part may be formed by the number from a counter that counts the number of meters of the web which have been unwound from a roll. Such counter is usually reset at zero at the starting of the treatment, for example coating, of each new web roll. Still another part may be formed by an identification number for the device that detected the object. The circuit comprises further a second trigger 61 that is directly connected with the input terminal 50 and that serves for the immediate signalling at a terminal 62 in the event of the occurrence of defects that are so severe that they need not a repeated circulation through the correlation circuit, with the corresponding delay, to reach a level at which sufficient signal to noise distinction has been obtained.

It should finally be noted that the duration of the active operation of the device, namely from a time $t_1$ to a time $t_{1024}$, is a fraction only of the period of one complete scanning.

The examination of the moving web thus occurs in interrupted fashion considered in the longitudinal direction. Taking into account however, that the device according to the invention is intended for the identification of streaklike defects of protracted duration, this lack of continuity of the measurement in the longitudinal direction of the web is without any importance.

Further details about the principle of operation of the device described hereinbefore, namely the scanning of a material across at least part of the width of its path by means of one more beams of radiation which or each at any given instant irradiates a narrow elongated zone (elongated in the direction of travel of the material) within the width of the path, receiving quanta of such radiant energy, modulated by adjacent successively irradiated zones of the material, on a photocell, deriving from such photocell a multiplicity of sequential signals each representative of a particular said zone, and comparing successive said signals with each other and using amplitude differences between compared signals as indicative of the presence of said defects, may be found in our co-pending British application No. 27,863/78 (which corresponds to U.S. application Ser. No. 50,792, filed June 21, 1979) entitled "Method and device for inspecting a moving sheet material for streaklike defects".

The basic operation of an additive correlator as used in the block circuit of FIG. 4 is illustrated in FIGS. 6 and 7.

Referring to FIG. 6 the circuit comprises an adder 67, a delay line 68 with a delay time $\tau$ and an adjustable feedback element 69 with a gain A comprised between 0 and 1. It can be shown that the relation between the output voltage $V_o$ and the input voltage $V_i$ is expressed by:

$$V_o = V_i \frac{1}{1-A}(1 - e^{-\frac{1-A}{\tau}t}) \quad (1)$$

and that the improvement of the S/N ratio is:

$$S/N = \sqrt{\frac{1+A}{1-A}} \quad (2)$$

or, expressed in db:

$$S/N = 10 \log \frac{1+A}{1-A} \quad (3)$$

The system reaches 99% of its maximum S/N improvement after a time t given by:

$$t = \frac{5 \cdot \tau}{1-A} \quad (4)$$

As mentioned already in the introduction of the specification, a significant improvement of the S/N ratio can only be obtained for a gain close to 1, e.g. 0.99, which requires in practice a digital system for stable operation. The time required for reaching such improved S/N ratio is not neglectable. For instance, for the device illustrated in FIGS. 1 to 4 wherein $\tau$ is equal to 0.2 s, the time will equal 100 sec.

$$\left(\text{from } t = \frac{5 \times 0.2}{1 - 0.99}\right).$$

FIG. 7 is a diagram illustrating the S/N improvement for A=0.99, $\tau$=0.2 s, and t=100 s. The S/N improvement amounts to a ratio of 14.106. The abscissa is a time axis in seconds whereas the ordinate represents $V_o$. The maximum level of the noise component $V_n$ of the output signal $V_o$ after 100 s has been arbitrarily illustrated at a level of 1 volt. In fact $$V_n = V_i \sqrt{\frac{1}{1-A^2}}$$

whereas $$V_d = V_i \sqrt{\frac{1}{1-A}}.$$

It may be seen that both the noise signal $V_n$ and the defect signal $V_d$ exponentially increase in the same direction towards a determined limit.

In accordance with the present invention, the S/N ratio of periodically recurring signals is improved by multiplicatively correlating said signals instead of additively correlating them. The basic operation of multiplicative correlation is illustrated in FIG. 8 wherein the block circuit comprises a multiplier (hereafter referred to as muliplicator) 70, a delay line 71 with a delay time $\tau$, and a feedback element 72 with a gain constant A. It can be shown that the relation between the output voltage $V_o$ and the input voltage $V_i$ is expressed by:

$$\left[ V_o = \pi_{i=0}^{\infty} A^i \cdot V_i(t - i \cdot \tau) \right]$$

In consequence, the system produces a S/N improvement that is infinitely great in theory. In practice, said improvement is limited by the maximal level the signal component $V_d$ can reach in the circuit. Common values for said signal $V_d$ are within 12 and 15 volts in modern integrated circuit lay-outs.

A basic condition for the operation of the described circuit is that the product of the input signal $V_i$ with its delayed equivalent is always greater than one. In case that product is smaller than one, then repeated multiplication will only reduce the amplitude of the signal instead of increasing it. The mentioned condition may be met in one of two ways: either the signal $V_i$ is greater than 1 volt and in that case the gain A may be equal to one, or the signal $V_i$ is smaller than one volt and in that case the gain A is adjusted so that the product $V_i \cdot A$ is greater than 1.

Another basic condition for the operation of the circuit is that the ratio of the useful signal level $V_d$ to the effective noise level $V_n$ of the input voltage $V_i$ be greater than one. Otherwise the system is incapable of making a distinction between signal and noise. The operation of the system is illustrated in the diagram of FIG. 9 wherein the abscissa is a time axis in seconds, and the ordinate represents the output voltage $V_o$. In case $V_i = 1$ volt and for $A = 1$, there is no S/N improvement whatsoever.

In case $V_i > 1$, than it may be seen that as a consequence of repeated multiplication the output voltage $V_o$ increases towards infinity. In practice this voltage $V_o$ will reach a limit $V_{sat}$ which is the saturation voltage or the full scale output voltage of the electronic circuit. In case $V_i < 1$, then the output voltage $V_a$ decreases as a consequence of repeated multiplication and tends towards zero. Thus it is clear that the signal component $V_d$ of $V_i$ should be greater than 1 whereas the effective noise component $V_n$ of $V_i$ should be smaller than 1.

FIG. 10 is a block circuit of a multiplicative correlator wherein common integrated circuits are used. A multiplier 75 (type 8013 manufactured by Intersil Corp.) is followed by an analogue to digital convertor 76 (type AD 7570 manufactured by Analog Devices), a digital 8-bit shift register 77 (type SY 2533 manufactured by Synertek) and a digital to analogue convertor 77 (type AD 559 manufactured by Analog Devices). The circuit comprises further an analogue adder 79 (type µA 741 manufactured by Fairchild) for adding to the output voltage $V_o$ a small voltage $V_a$ that may be set by means of a potentiometer 80.

The purpose of voltage $V_a$ is as follows. At the starting of a correlation cycle, it may occur that, depending on the offset characteristics of the convertor 78, that the output voltage $V_o$ is zero. The repeated multiplication of $V_o$ by $V_i$ will involve no result since multiplication by a factor zero gives a product that remains zero.

Therefore, in order to take account of the possibility that the output voltage $V_o$ might be zero, a given voltage $V_a$ is added to the voltage $V_o$ before the multiplication with $V_i$ occurs. Voltage $V_a$ may be small since its only purpose is to make sure that $V_i$ will not become multiplied by zero. In practice, $V_a$ will be chosen between 100 and 200 mV for a full scale output voltage for the device of 10 V. It is clear that the addition of voltage $V_a$ "falsifies", so to say, the correlated output signal $V_o$. It should be understood, however, that this "falsification" is neglectable as compared to the distortion of the signal $V_i$ as a consequence of the multiplicative correlation. As a matter of fact, any signal $V_i$ that comprises a signal component greater than 1 volt and a noise component smaller than 1 volt, inevitably is amplified after a number of correlations to the saturation voltage $V_{sat}$ of the device. Thus, whether the signal component of $V_i$ is, for instance, 1.1 or 1.5 V, the output voltage $V_o$ will become within the shortest time equal to $V_{sat}$. The described distortion of the input signal $V_i$ is, however, quite immaterial in this type of apparatus which has only the purpose of increasing the S/N ratio of a signal $V_i$ as rapidly and as much as possible.

Even if the signal component $V_d$ of a signal $V_i$ is smaller than 1 V, it is still possible to multiplicatively correlate said signal in amplifying it by a factor A so that the product of $V_i \cdot A$ is greater than 1. An amplifier for carrying out the mentioned step is illustrated in broken lines by the block 81 in FIG. 10. Said block might as well figure between the input terminal 82 of the circuit and the multiplier 75, between the multiplier 75 and the convertor 76, etc., thereby to provide at the lower input terminal of the multiplier 75 an input signal greater than 1 V.

FIG. 11 illustrates the device described hereinbefore with reference to FIGS. 1 to 4, modified however, for multiplicative correlation of the measurement signal $V_m$. The part of the drawing situated at the left hand side of the dash and dot line 49 is identical with that of FIG. 4 and has therefore been given the same reference numerals, except for the amplifiers 44 the gain of which has been made adjustable, as indicated by the conventional sign, so that the output measurement signals $V_m$ at terminals 50 may be so adjusted that the noise component of the signal at each terminal 50 is just smaller than 1 volt.

The signals $V_m$ form in fact the input signals $V_i$ of the multiplicative correlator, the shift register 77 of which is controlled synchronously with the scanning of the different sections of the web by means of the output signal from the pulse shaper 57. The correlator is followed by two comparators 58 and 61 that have the same function as the comparators disclosed in FIG. 4. The source 80 has been adjusted for adding a signal $V_a = 0.2$ V to the output signal $V_o$. The following data illustrate the operation of the described device that was used for the inspection of a wet coating of silver halide that was applied by means of a slide hopper to a polyethylene terephthalate film having a width of 1.70 m.

| | |
|---|---|
| Scanning amplitude d of the frame 10 | 35 cm |
| Effective scanning width c | 21.5 cm |
| Oscillation period P | 2.4 s |
| Effective scanning time T | 0.6 s |
| Number of optical units | 8 |
| Width of a line of radiant energy on | |

| -continued | |
|---|---|
| the web | 1 mm |
| Length of a line of radiant energy | 10 cm |
| Distance between the two lines of a pair of lines | 1 mm |
| Frequency (f) of the oscillator 43 (that is also the inspection frequency) | 10 kHz |
| Number of signal comparisons during one scan (Txf) | 6000 |
| Number of signal observations during one scan | 1024 |
| Number of signal circulations through a correlator | 5 |
| Corresponding observation time | 12 s |
| S/N improvement obtained by additive correlation according to FIG. 4 | 12.79 db (for attenutation A = 0.9) |
| S/N improvement obtained by multiplicative correlation according to FIG. 11 | 42.14 db (for 8 bit resolution of the AD convertor) |
| Variation in the output signals for a film fluttering of 1 mm at a frequency above 20 Hz: 0.5% | |
| Components used: | |
| Lamps 35 and 36: LED type GE manufactured by FIRE DIVISION International Audio Visual Inc. | |
| Photocells 18: PIN-L4 manufactured by United Detector Technology | |
| Spectral band of measurement: 880 nm wavelength. | |

It should be noted that the multiplicity of signal comparisons, namely 6000, that is carried out by the measuring device with the alternately operated pairs of lamps 95 and 96, is much greater than the number, namely 1024, of discrete signals into which the output voltage $V_o$ of the measuring device is divided for carrying out the correlation. It can thus be said that finally the resolving power of the device is 1024 points for each web section being examined. Whereas this number is largely sufficient for many applications, it should be understood it can easily be increased by using instead of pulse strip 46 another pulse strip capable of producing a larger number of pulses. It is evident that the number of the positions of the shift register 77 should correspondingly be increased. Another point that has to do with the sensitivity of the device is that the A/C convertors 75 and the D/C convertors 78 are 8 bit devices whereby 256 (that is $2^8$) distinct levels of the signals $V_i$ can be transmitted. It is clear that by using convertors with a number of bits $2^n$, wherein n is greater than 8, the sensitivity for small signal variations can further be increased.

In order to visualize the S/N ratio improvement that can be obtained in accordance with the present invention, the following test was made. A generator for generating a white noise containing frequencies within the range of 0 to 20 kHz was used to similate the input voltage $V_i$ of a correlator. The amplitude was so adjusted that the effective noise level was slightly less than 1 volt. This noise signal is the signal 85 in FIG. 12 which figure is a reproduction of an instant picture of the screen of an oscilloscope on which the different signals were made visible. The grid of the oscilloscope, which has been overdrawn for the sake of visibility, is composed of squares measuring 1×1 cm. The vertical sensitivity was adjusted so that 1 cm corresponds with 1 volt. The time basis was adjusted so that 1 cm of deflection in the horizontal direction corresponds with a time interval of 10 ms. The signal 86 represents an arbitrarily produced defect pulse 90 with a level slightly greater than 1 volt. The signal 87 is the sum of signals 85 and 86. It should be understood that the three signals were not simultaneously displayed on the oscilloscope, but that three successive pictures were taken on one film with the vertical positioning of the cathode ray spot so adjusted that for each signal a different vertical position on the screen was taken.

The result of a S/N ratio improvement of the signal 87 by 12.79 db as a consequence of additive correlation is illustrated by the curve 88 of FIG. 13 wherein the vertical sensitivity was 1 V/cm, whereas the quite spectacular improvement of 42.14 db by multiplicative correlation is illustrated by the curve 89 wherein the vertical sensitivity was 10 V/cm.

It will be understood that the invention is not limited to the described embodiment.

It is possible to use the known additive correlation in cascade with the inventive multiplicative correlation to further improve the S/N ratio, and thereby the sensitivity of the system for streaklike defects.

It is further possible to produce the measurement signal $V_m$ in another way, namely by scanning each section of the width of the web by only one light source, and by delaying the signal produced by said light source over a certain time thereby to compare it with the instant signal after such delay time in order to establish an occasional deviation. This technique of simulating the second light source of each pair of sources is disclosed in detail in our co-pending application Ser. No. 27,863/78 referred to hereinbefore.

It is also possible to correlate the output voltages $V_p$ of the photocells after suitable amplification, and then to compare them with a suitable reference signal, "normalized" as the case may be as mentioned in the introduction of the specification.

Other types of delay lines may be used in the correlator, for instance magnetic delay lines, acoustic delay lines, charge coupled devices (CCD's) etc.

We claim:

1. In a method for inspecting at least one longitudinal section of a moving sheet material for streaklike defects, by repeatedly transversely scanning during a period P each such section of the material by means of radiant energy capable of being modulated by said sheet material, and by receiving said modulated energy on at least one photocell thereby to produce at said at least one photocell at least one train of measurement signals $V_m$ periodically recurring in response with the scanning of the material and which vary in intensity as an indication of the presence of said defects, wherein the S/N ratio of those having a S/N ratio of greater than one is improved by electronic correlation, the improvement wherein said correlation comprises the following steps:

delaying the measurement signals $V_m$ in the train during one scan over a time delay t corresponding with the scanning period P;

multiplying the measurement signals during a following scan with a factor that is proportional to the corresponding delayed signals, and is greater than 1;

delaying the thus multiplied signals over said time delay t and multiplying the measurement signals produced during a subsequent scan with a factor that is proportional to said corresponding previous multiplied signals, and so on for a number of scanning periods.

2. The method according to claim 1, wherein said proportional factor is the product of the previous signals and a constant A which is at least equal to one.

3. Method according to claim 1, comprising the step of adding a constant signal $V_a$ to said delayed signals, said signal $V_a$ being comprised between zero and $V_m$.

4. Method according to claim 1, comprising generating a multiplicity of discrete measurement signals during each scanning, comparing each two successive discrete measurement signals with each other and using the difference between each such two successive signals as the signal $V_m$ the S/N ratio of which must be improved.

5. Method according to claim 1, wherein the delay over said period P of each signal $V_m$ or of each already multiplied signal $V_x$ occurs by means of a digital delay line which is controlled in response to the scanning of the sheet material.

6. Method according to claim 1, comprising continuing the repetition of the multiplication of each delayed signal $V_m$ until a predetermined output voltage $V_o$ has been obtained.

7. Method according to claim 6, wherein said predetermined value is the saturation voltage of the electronic circuitry for carrying out said correlation.

8. In an apparatus for inspecting a moving sheet material for streaklike defects, comprising cooperating radiant energy means and photocell means arranged for periodically scanning said moving sheet material, means for amplifying the measurement signals $V_m$ that are produced during each scan of the sheet material, and electronic correlation means for improving the S/N ratio of the measurement signals, the improvement wherein said electronic correlation means comprises:

delay lines controlled in response to the scanning of the material for delaying said measurement signals $V_m$ over a delay period equal to the scanning period P;

multipliers for multiplying the delayed signals $V_m$ with corresponding subsequent measurement signals $V_m$ that occur during a following scanning period, and for repeating such multiplication for a number of periods thereby to increase the S/N ratio of those measurement signals having a signal component $V_d$ greater than the effective noise component $V_n$, and means for evaluating said signals $V_d$ with improved S/N ratio thereby to identify streaklike defects in the sheet material.

9. Device according to claim 8, wherein said correlation means includes a feedback line between the output of said delay line and the input of said multiplier, and further comprises an adder in said feedback line for adding to the fed back signal an adjustable signal greater than zero.

10. Device according to claim 8 having a plurality of separate measurement channels and wherein an amplifier with adjustable gain is provided for each measurement channel, thereby to adjust each measurement signal $V_m$ in such a way that the noise component $V_n$ thereof is smaller than 1 volt but that the signal component $V_d$ is greater than 1 volt.

* * * * *